(12) United States Patent
Krieg

(10) Patent No.: US 8,380,283 B2
(45) Date of Patent: Feb. 19, 2013

(54) METHOD FOR VISUALLY MONITORING AN IRREVERSIBLE ELECTROPORATION TREATMENT, AND MAGNETIC RESONANCE IMAGING APPARATUS WITH INTEGRATED ELECTROPORATION TREATMENT DEVICE

(75) Inventor: Robert Krieg, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 520 days.

(21) Appl. No.: 12/491,559

(22) Filed: Jun. 25, 2009

(65) Prior Publication Data

US 2009/0326366 A1   Dec. 31, 2009

(30) Foreign Application Priority Data

Jun. 25, 2008 (DE) .................... 10 2008 030 242

(51) Int. Cl.
*A61B 5/05* (2006.01)
(52) U.S. Cl. ......................................................... 600/411
(58) Field of Classification Search .......... 600/410–411, 600/427, 439
See application file for complete search history.

(56) References Cited

U.S. PATENT DOCUMENTS

| | | | |
|---|---|---|---|
| 6,272,370 B1 | 8/2001 | Gillies et al. | |
| 7,643,864 B2 * | 1/2010 | Elgort et al. | 600/410 |
| 2004/0143181 A1 * | 7/2004 | Damasco et al. | 600/411 |
| 2005/0059878 A1 * | 3/2005 | Winter | 600/410 |
| 2005/0283215 A1 | 12/2005 | Desinger et al. | |
| 2006/0264752 A1 * | 11/2006 | Rubinsky et al. | 600/439 |
| 2006/0264807 A1 * | 11/2006 | Westersten et al. | 604/21 |
| 2007/0020326 A1 | 1/2007 | Walker et al. | |
| 2009/0118610 A1 | 5/2009 | Karmarkar et al. | |

FOREIGN PATENT DOCUMENTS

DE   44 33 502 A1   3/1996

OTHER PUBLICATIONS

"Irreversible Electroporation in Medicine," Rubinsky Technology in Cancer Research and Treatment, vol. 6, No. 4 (2007), pp. 255-259.
"Improvement of Midbrain Nuclei Susceptibility Contrast in T1-weighted SPGR for Image Guided Deep Brain Stimulation," Chen et al., Proc. Intl. Soc. Mag. Reson. Med., vol. 16 (2008) p. 3515.

* cited by examiner

*Primary Examiner* — Brian Casler
*Assistant Examiner* — Christopher Cook
(74) *Attorney, Agent, or Firm* — Schiff Hardin LLP

(57) ABSTRACT

In a method for implementing an irreversible electroporation treatment with an electroporation device having at least two treatment electrodes, magnetic resonance exposures are acquired for visual monitoring of the treatment, and magnetic resonance-compatible electrodes are used as treatment electrodes. A magnetic resonance imaging apparatus has an electroporation device integrated therein, so as to be operable by co-use of at least some of the same components that arte used for image data acquisition.

14 Claims, 1 Drawing Sheet

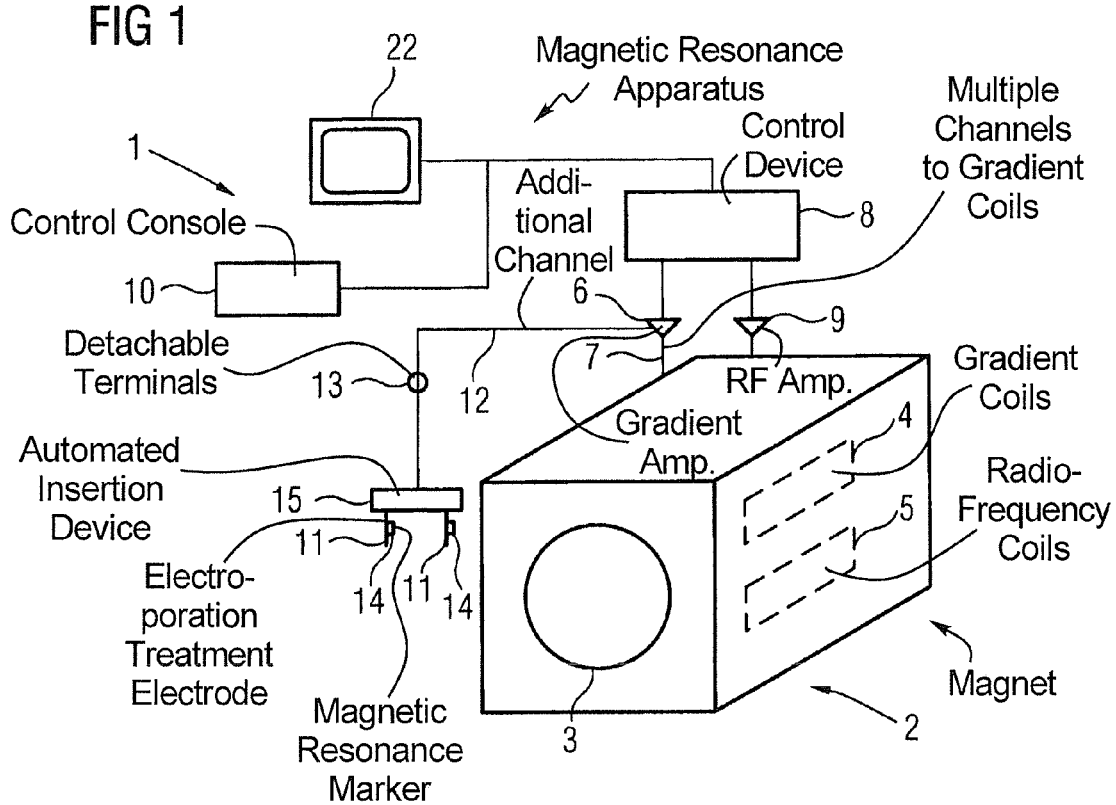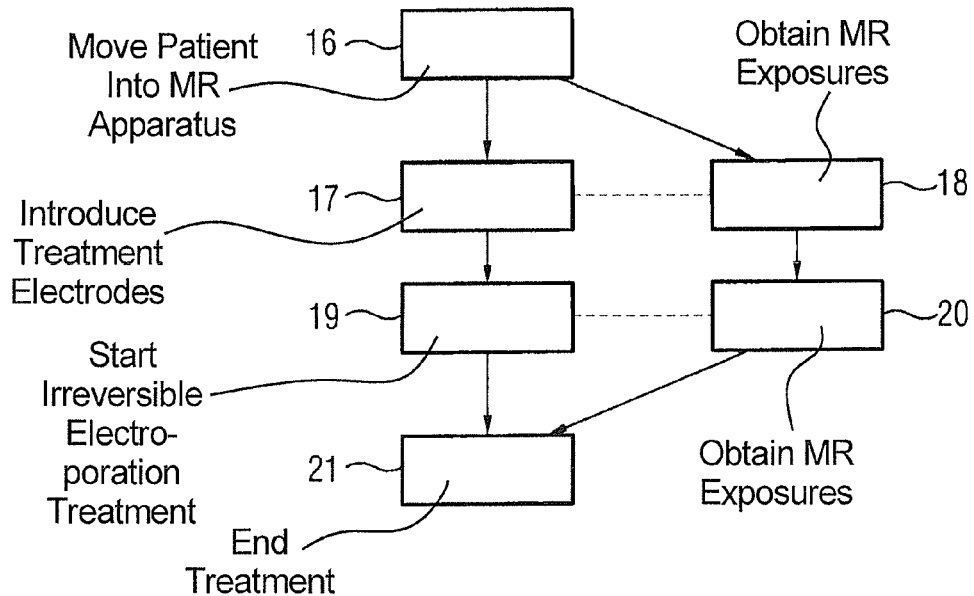

METHOD FOR VISUALLY MONITORING AN IRREVERSIBLE ELECTROPORATION TREATMENT, AND MAGNETIC RESONANCE IMAGING APPARATUS WITH INTEGRATED ELECTROPORATION TREATMENT DEVICE

BACKGROUND OF THE INVENTION

1. Field of the Invention

The invention concerns a method for visual monitoring of an irreversible electroporation treatment with an electroporation device of the type having at least two treatment electrodes, as well a device operating according to such a method.

2. Description of the Prior Art

Minimally invasive procedures for diagnosis and therapy are gaining ever greater importance in medicine. They are characterized by the operating medical personnel or the physician having no direct view of the positioning process or even of the treatment progress, such that it is typical to use a visual monitoring system in such methods.

In many methods, for example radio-frequency ablation, penetrating radiation-based systems are used for this purpose, in particular in x-ray tomography and even computed tomography. This has the disadvantage that both the patient and the personnel conducting the procedure are exposed to a high radiation dose. Moreover, x-ray-based visual monitoring is not suitable for all procedures that are desired to be observed.

Irreversible electroporation has recently been proposed as a new minimally invasive method, in particular for the treatment of tumors. Electroporation is a phenomenon that basically triggers a rise in the permeability of the cell membrane when electrical fields are applied briefly (for instance in the range from microseconds to milliseconds). If low fields are applied, the defects arising in the membrane close again, such that this type of electroporation is called reversible electroporation. This is widely used in methods to insert genes or even to introduce anti-cancer medications (for example bleomycin).

However, if stronger fields are applied that cause the defects arising in the cell membrane not to close again, this is designated as irreversible electroporation. Irreversible electroporation ultimately leads to cell death since the self-regulation mechanisms of the cells are lost. For achieving this, it is now proposed to introduce at least two electrodes into the body, for example applied at the tumor to be treated, and to achieve there a cell necrosis by irreversible cell membrane permeabilization. Bipolar electroporation pulses that in particular have a voltage in the range of a few kilovolts and, for instance, are applied approximately 10 times in a time interval of one second are typical. Eight 2,500 volt pulses of a duration of 100 microseconds can be used, for example, between which a pause of 100 milliseconds respectively exists. For an overview of irreversible electroporation in medicine, refer to the article "Irreversible Electroporation in Medicine" by Boris Rubinsky, Technology in Cancer Research and Treatment, Volume 6, 2007, Pages 255-259.

To monitor irreversible electroporation treatment it has been proposed to use an ultrasound device in order to monitor the positioning of the electroporation electrodes. However, this is not a very precise monitoring modality, and it requires additional activity on the part of the personnel administering the treatment.

An object of the present invention is to provide a method that allows an improved visual monitoring of an irreversible electroporation treatment.

This object is achieved in a method of the aforementioned type wherein, according to the invention, magnetic resonance exposures are acquired for visual monitoring, and magnetic resonance-compatible electrodes are used as treatment electrodes.

Magnetic resonance has proven to be a method that is ideally suited to serve for monitoring of an electroporation treatment. This is particularly true since the electroporation method implemented with direct current pulses has proven to be magnetic resonance-compatible (in contrast to other known, invasive methods, for example radio-frequency ablation). However, magnetic resonance-compatible electrodes must be used. Such electrodes are known in principle in the prior art and are used, for example, in "deep brain stimulation" (see also N-K. Chen and G. S. Young, "Improvement of midbrain nuclei susceptibility contrast in T1-weighted SPGR for image-guided deep brain stimulation", Proc. Intl. Soc. Mag. Reson. Med. 16 (2008), Page 3515). No disruptions of the magnetic resonance acquisitions arise through the use of such magnetic resonance-compatible electrodes or in the implementation of the treatment itself, such that the monitoring can ensue at a high quality. Moreover, the high strength magnetic resonance field has no effect on the efficacy of the treatment. By the use of magnetic resonance it is therefore advantageously avoided that a contamination of the patient and the operating personnel or an excessive additional exposure for the treatment personnel occurs. It is additionally possible to produce more precise, high-quality visual monitoring exposures and to show them immediately.

With the method according to the invention it is naturally possible that the introduction of the treatment electrodes at the treatment location is visually monitored. In this way it can be checked whether the treatment electrodes are correctly positioned so that ultimately only tissue to be necrotized lies between them.

However, given use of magnetic resonance for visual monitoring, the treatment progress can also advantageously be visually monitored. For this purpose, diffusion exposures are advantageously produced for visual monitoring of the treatment progress. The protons achieve a greater mobility due to the triggering of the cell structures during the programmed cell death (also called apoptosis), such that this effect can be measured via diffusion-weighted magnetic resonance sequences. According to the method according to the invention, how far the killing of the malignant cells has already progressed can be directly observed in this way using the magnetic resonance visual monitoring.

While, within the scope of the method according to the invention, it is also naturally possible to acquire the magnetic resonance exposures in pauses between different application segments and/or in treatment pauses so that the patient is treated outside of the magnetic resonance device if necessary (whereupon the patient is inserted into the magnetic resonance device in treatment pauses) It is also possible in a preferred manner with the method according to the invention to acquire the magnetic resonance exposures in parallel with the introduction of the treatment electrodes and/or parallel to the treatment process. In this way the patient is located within the patient receptacle of the magnetic resonance device at all times so that a tracking of the introduction and/or of the treatment in real time is in particular also enabled.

If the electroporation treatment should be conducted entirely while the patient is located within the patient receptacle of a magnetic resonance system being used, the treatment electrodes (in particular fashioned as needle electrodes) are automatically brought to the treatment location by the insertion device. Given the use of such devices, two or four needle electrodes are frequently provided that can be driven out from a device (which can be placed on the patient, for example) to a defined position at a defined depth. Here it is in particular advantageous when an insertion device is used that essentially consists of non-magnetic materials.

When the introduction process (and thus the position of the treatment electrodes) is to be monitored via the magnetic resonance exposures, it can be provided that treatment electrodes provided with magnetic resonance markers or electrode mounts provided with magnetic resonance markers are used.

The visual monitoring in the method according to the invention can ensue continuously or intermittently, such that how the tissue alters (for example) can be observed continuously; however, this can occur just as well at fixed time intervals.

In addition to the method, the invention also encompasses a magnetic resonance device with an integrated electroporation device.

Through such an integration, additional advantages can be achieved in addition to achieving the advantages that the method according to the invention for visual monitoring by means of magnetic resonance exposures already offers. Such a solution is in particular cost-effective since fewer structural elements are necessary. This already results from the high technical compatibility of the two devices. In such a magnetic resonance device the spatial separation between the two devices is advantageously entirely done away with, such that both the treatment and the visual. monitoring of the same can ensue without problems with a single modalities.

The magnetic resonance device can have magnetic resonance-compatible treatment electrodes fashioned for reversible electroporation treatment. These are ultimately already sufficient as additional technical components because, in an additional, particularly advantageous embodiment (since the magnetic resonance device has a gradient amplifier to activate multiple gradient coils of associated channels and a control device for generation of pulse sequences anyway) to control the treatment electrodes via an additional channel via the gradient amplifier. The control device for activation of the gradient amplifier is fashioned to output an electroporation pulse sequence via the additional channel. It was additionally recognized that the components that are required in an electroporation device are already present in a suitable form in a magnetic resonance device. As described earlier, irreversible electroporation is also based on a specific pulse sequence (the electroporation pulse sequence) that is applied at the electrodes for the treatment. However, the control device of a magnetic resonance device is fashioned precisely to generate and process such pulse sequences anyway in order to activate the gradient coils and radio-frequency coils. In addition to this, most voltages required in irreversible electroporation are in the range of a few kilovolts. Voltages of this magnitude are also required to activate the gradient coils and are accordingly generated by the gradient amplifier. These realizations are now advantageously utilized according to the invention in order to allow a particularly advantageous integration of the electroporesis device into the magnetic resonance device. The components that are present anyway in the magnetic resonance device are advantageously also used for the electroporation treatment, such that ultimately no additional technical devices or items of equipment are required except for the treatment electrodes. Only one additional output at the gradient amplifier for one additional, low-amperage channel and a corresponding design of the gradient amplifier and the control device are required. The additional sequencer normally necessary for electroporation treatment, as well as the amplifier for the voltages in the kilovolt range, are no longer additionally required, such that costs are saved and additional advantages are achieved in addition to the integration effect already cited above.

In another embodiment of the magnetic resonance device, terminals can be provided via which the treatment electrodes can be connected to the magnetic resonance device such that they can be detached. It is accordingly possible to remove the treatment electrodes as long as they are not required and only "normal" acquisitions should be executed with the magnetic resonance device.

To simplify the visual monitoring of the position of the treatment electrodes or their mounts, the treatment electrodes or the treatment electrode mounts supporting the treatment electrodes in the body of a patient are provided with magnetic resonance markers (for example coils or the like).

As also already addressed with regard to the method according to the invention, the magnetic resonance device can include an insertion device (controllable via the control device) to introduce the treatment electrodes (fashioned in particular as needle electrodes) at the treatment location. Such devices, known from the prior art, are (for example) placed on the patient and contain treatment electrodes (for example two or four pieces) that can be driven out up to a defined depth at a defined position. Such an insertion device enables the automatic introduction of the treatment electrodes at the treatment location, which then can in particular ensue inside the magnetic resonance device. The insertion device can advantageously consist essentially of non-magnetic materials.

An embodiment in which a control unit of the magnetic resonance device is fashioned to operate the electroporation device is particularly advantageous. An operator can then centrally execute all functions from one control unit, thus both the functions pertaining to the electroporation treatment and the functions necessary for visual monitoring.

BRIEF DESCRIPTION OF THE DRAWINGS

FIG. 1 schematically illustrates a magnetic resonance apparatus according to the invention.

FIG. 2 is a flowchart of an embodiment of the method according to the invention

DESCRIPTION OF THE PREFERRED EMBODIMENTS

FIG. 1 shows a magnetic resonance apparatus 1 according to the invention in a basic schematic illustration. The apparatus 1 has a magnet 2 with a patient receptacle 3 into which a patient bed (not shown here) can be driven. Here the gradient coils 4 and the radio-frequency coils 5 are indicated only schematically. A gradient amplifier 6 is provided to activate the gradient coils 4, which gradient amplifier 6 activates the gradient coils 4 via multiple output channels 7 according to the pulse sequences created in a control device 8. A radio-frequency amplifier 9 is analogously provided for the radio-frequency coils 5. The magnetic resonance apparatus 1 also has a monitor 22 to display magnetic resonance exposures and additional information, as well as a control console 10 via which the necessary adjustments (settings) can be made.

The magnetic resonance apparatus 1 according to the invention has an integrated electroporation device that can also be directly operated via the control unit 10. The electroporation device serves for the implementation of an irreversible electroporation treatment, for example to necrotize the cells of a tumor. While an independent electroporation device requires a sequencer to generate the electroporation pulse sequences as well as an amplifier to activate treatment electrodes, with the present invention an integration is achieved by the control device 8 additionally serving as a sequencer for the electroporation sequence, and the gradient amplifier 6 additionally serving to activate single treatment electrodes 11 additionally required in the magnetic resonance apparatus 1. The control device 8 is accordingly additionally configured (compared to its configuration for conventional imaging) to process electroporation pulse sequences (received from the control console 10, for example), and the gradient amplifier 6 has an additional channel 12 for the activation of the treatment electrodes 11. This is achievable without problems since both the voltages required for irreversible electroporation treatment and the voltages necessary for activation of the gradient coils 4 are in the range of a few kilovolts.

The treatment electrodes 11 are connected with the magnetic resonance device via terminals 13 such that the electrodes 11 can be detached so that the treatment electrodes 11 can be temporarily removed from the magnetic resonance apparatus 1 when they are not required. The treatment electrodes 11 are additionally provided with magnetic resonance markers 14 that allow a more distinct detection capability in magnetic resonance exposures. Such markers 14, however, are not absolutely necessary.

The treatment electrodes 11 (which are usually fashioned as needle electrodes) can be manipulated in a defined manner (likewise controlled via the control device 8) from an insertion device 15 consisting essentially of non-magnetic materials, in order to insert said treatment electrodes 11 at a treatment location. In this way the treatment electrodes 11 can be automatically brought to the treatment location, in particular when the patient is located within the patient receptacle.

The treatment electrodes 11 are additionally fashioned so as to be magnetic resonance-compatible, meaning that they can be employed in the strong fields of the magnet 2, and also do not interfere with the image acquisition with the magnetic resonance device 1.

The method according to the invention, which is explained in detail through the flowchart in FIG. 2, can now be executed through and with the magnetic resonance apparatus 1. Basically, an electroporation treatment is visually monitored via magnetic resonance acquisitions, and the magnetic resonance-compatible treatment electrodes 11 are used in the treatment.

In Step 16, the patient is initially moved into the patient receptacle 3 after the insertion device 15 has been correspondingly positioned on him. Overview exposures can likewise be produced in Step 16 as well in order to check the position of the insertion device 15.

The treatment electrodes 11 are then introduced at the treatment location in the patient in Step 17. In parallel to this (Step 18), magnetic resonance exposures are produced for monitoring the insertion process. This is possible without problems since the patient is located in the patient receptacle 3 anyway. The treating personnel can even observe in real time (or intermittently at defined time intervals as well) whether the treatment electrodes 11 have arrived at the correct location.

If and when this occurs the irreversible electroporation treatment is started in Step 19 by appropriate electroporation pulse sequences being provided to the treatment electrodes 11 via the control device 8 and the gradient amplifier 6. Furthermore, magnetic resonance exposures are produced in parallel to this (Step 20) in order to observe the treatment progress. These are preferably diffusion image exposures that show the mobility of the protons in the treated cells designated for programmed cell necrotization. The gradient coils 4 and radio-frequency coils 5 are thus activated with different sequences than at the time of the insertion procedure. The exposures acquired for visual monitoring are in turn shown on the monitor 22 to allow the treating personnel the opportunity to modify the course of the therapy at any time via the control unit 10. When the treatment is ended, the treatment electrodes 11 are removed again from the patient via the insertion device 15 and the procedure is terminated (Step 21).

Naturally, the invention is not limited to the exemplary embodiments shown herein. For example, the treatment electrodes can also be inserted into the patient in a different minimally invasive manner, in particular on electrode mounts attached via a cathode or the like. Moreover, magnetic resonance markers can also be provided at the electrode mounts. In principle, it is even conceivable to implement the method according to the invention not with the integrated magnetic resonance device 1 but rather to use a separate magnetic resonance device and electroporation device, wherein the patient is then inserted into the patient receptacle after individual treatment steps in order to acquire the magnetic resonance exposures, then remove the patient again and continue the treatment.

Although modifications and changes may be suggested by those skilled in the art, it is the intention of the inventor to embody within the patent warranted hereon all changes and modifications as reasonably and properly come within the scope of his or her contribution to the art.

I claim as my invention:

1. A method for implementing an irreversible electroporation treatment, comprising the steps of:
   placing a patient in a magnetic resonance imaging apparatus comprising a plurality of components that participate in acquisition of magnetic resonance image data from the patient said plurality of components including a gradient amplifier and multiple gradient coils supplied with power from said gradient amplifier via a plurality of channels respectively for said multiple gradient coils, and a control device configured to generate pulse sequences supplied to said gradient amplifier to operate said multiple gradient coils in said acquisition of magnetic resonance image data from the patient;
   providing said gradient amplifier with an additional channel, that is not used in said acquisition of magnetic resonance image data from the patient, and connecting said additional channel to at least two magnetic resonance-compatible irreversible electroporation treatment electrodes;
   conducting an irreversible electroporation treatment of the patient in the magnetic resonance imaging apparatus by physical interaction of said at least two magnetic resonance-compatible irreversible electroporation treatment electrodes with said patient, using an electroporation pulse sequence, supplied by said control device via said additional channel to said magnetic resonance-compatible treatment electrodes; and
   during said irreversible electroporation treatment, obtaining magnetic resonance exposures of the patient using said magnetic resonance imaging apparatus, including interaction with said magnetic resonance-compatible irreversible electroporation treatment electrodes, and visually monitoring said irreversible electroporation treatment using said magnetic resonance exposures.

2. A method as claimed in claim 1 comprising using said magnetic resonance exposures to monitor progress of said irreversible electroporation treatment.

3. A method as claimed in claim 2 comprising obtaining diffusion exposures as said magnetic resonance exposures.

4. A method as claimed in claim 1 comprising acquiring said magnetic resonance exposures in parallel with insertion of said magnetic resonance-compatible irreversible electroporation treatment electrodes, or in parallel with another part of said irreversible electroporation treatment.

5. A method as claimed in claim 1 comprising automatically manipulating said magnetic resonance-compatible irreversible electroporation treatment electrodes in said irreversible electroporation treatment using an automated insertion device.

6. A method as claimed in claim 5 comprising employing an insertion device composed substantially of non-magnetic materials.

7. A method as claimed in claim 1 comprising providing said magnetic resonance-compatible irreversible electroporation treatment electrodes with magnetic resonance markers, and placing said markers at a site selected from the group consisting of on the magnetic resonance-compatible irreversible electroporation treatment electrodes themselves, and on an electrode mount for the magnetic resonance-compatible irreversible electroporation treatment electrodes.

8. A method as claimed in claim 1 comprising implementing said visual monitoring continuously or intermittently.

9. A magnetic resonance imaging apparatus comprising:
a magnetic resonance data acquisition device configured to receive a patient therein to acquire a magnetic resonance image data from the patient;
said magnetic resonance data acquisition device comprising a plurality of components that participate in acquisition of said magnetic resonance image data from the patient in the magnetic resonance data acquisition device, said plurality of components including a gradient amplifier and multiple gradient coils supplied with power from said gradient amplifier via a plurality of channels respectively for said multiple gradient coils, and a control device configured to generate pulse sequences supplied to said gradient amplifier to operate said multiple gradient coils in said acquisition of said magnetic resonance image data from the patient;
an electroporation treatment device configured to implement an irreversible electroporation treatment on the patient in the magnetic resonance data acquisition device;
said electroporation device comprising a plurality of components that participate in said irreversible electroporation treatment, including at least two magnetic resonance-compatible treatment electrodes configured to interact with the patient to implement said irreversible electroporation treatment;
said electroporation device being integrated with said magnetic resonance data acquisition device, and said gradient amplifier comprising an additional channel, that is not used in said acquisition of said magnetic resonance image data from the patient, connected to said at least two magnetic resonance-compatible treatment electrodes; and
said control device being configured to operate said electroporation device to implement said irreversible electroporation procedure on the patient using an electroporation pulse sequence, supplied by said control unit via said additional channel to said magnetic resonance-compatible treatment electrodes and, during said irreversible electroporation treatment, to operate said magnetic resonance imaging apparatus to obtain magnetic resonance exposures of the patient and to visually display said exposures to allow monitoring of said electroporation treatment using said magnetic resonance exposures.

10. A magnetic resonance apparatus as claimed in claim 9 wherein said magnetic resonance-compatible treatment electrodes comprise terminals allowing detachable connection of said magnetic resonance-compatible treatment electrodes to said additional channel of said gradient amplifier.

11. A magnetic resonance apparatus as claimed in claim 9 wherein said magnetic resonance-compatible treatment electrodes comprise treatment electrode mounts that respectively support the magnetic resonance-compatible treatment electrodes in the body of the patient, and wherein said electroporation device comprises magnetic resonance markers located at a site selected from the group consisting of said magnetic resonance compatible treatment electrodes and on said treatment electrode mounts.

12. A magnetic resonance apparatus as claimed in claim 9 wherein, among said components that participate in said irreversible electroporation treatment, said electroporation device comprises an automated insertion device configured to automatically manipulate said magnetic resonance-compatible treatment electrodes relative to a treatment site of said irreversible electroporation treatment.

13. A magnetic resonance apparatus as claimed in claim 12 wherein,
said control device is configured to operate said automated insertion device to control manipulation of said magnetic resonance-compatible treatment electrodes in said irreversible electroporation treatment.

14. A magnetic resonance apparatus as claimed in claim 12 wherein said automatic insertion device is comprised substantially of non-magnetic materials.

* * * * *